United States Patent [19]

Kurane et al.

[11] Patent Number: 4,772,333
[45] Date of Patent: Sep. 20, 1988

[54] PREPARATION AND METHOD FOR BIOPRECIPITATION OF SOLUBLE PIGMENT IN AQUEOUS SOLUTION

[75] Inventors: Ryuichiro Kurane; Tomoo Kazuo, both of Ibaraki, Japan

[73] Assignees: Agency of Industrial Science and Technology; Ministry of International Trade and Industry, both of Tokyo, Japan

[21] Appl. No.: 31,373

[22] Filed: Mar. 30, 1987

[30] Foreign Application Priority Data

Nov. 14, 1986 [JP] Japan .............................. 61-272583
Nov. 14, 1986 [JP] Japan .............................. 61-272584

[51] Int. Cl.$^4$ ............................................. C07B 63/00
[52] U.S. Cl. .................................... 106/493; 106/501
[58] Field of Search ...................... 106/309, 288 Q, 20, 106/22, 23

[56] References Cited

U.S. PATENT DOCUMENTS 2,772,984 12/1956 Helfaer .
3,542,758 11/1970 Hegar .

*Primary Examiner*—Amelia Burgess Yarbrough
*Attorney, Agent, or Firm*—Oblon, Fisher, Spivak, McClelland & Maier

[57] ABSTRACT

From the aqueous solution of a soluble pigment, removal of the soluble pigment is attained by intimately mixing the aqueous solution, in the presence of an inorganic salt, with the product of microorganic culture obtained by culturing a bacterium belonging to genus Rhodococcus and allowing the resultant mixture to stand at rest thereby causing the pigment to flocculate and precipitate therein.

15 Claims, 2 Drawing Sheets

PREPARATION AND METHOD FOR BIOPRECIPITATION OF SOLUBLE PIGMENT IN AQUEOUS SOLUTION

BACKGROUND OF THE INVENTION

1. Filed of the Invention

This invention relates to a preparation for bioprecipitation of a soluble pigment in an aqueous solution and to a method for the treatment of the pigmented aqueous solution by the use of the preparation.

2. Description of the Prior Art

Substantially no effective method has been available to date for the removal of a water-soluble pigment from an aqueous solution. Barely a method which effects this removal by virtue of adsorption of the dissolved pigment on activated carbon has been resorted to heretofore. Another conventional method treats the pigmented aqueous solution with a bleaching agent not to remove the dissolved pigment but to whiten it. The former method requires to use the activated carbon in a large amount and entails a heavy cost and, therefore, fines utility only in special applications. The latter method only serves to decolorize apparently the pigmented solution and, therefore, suffers the principle of the soluble pigment, a coloring matter, to remain dissolved in the aqueous solution The soluble pigment cannot be removed by any physical means like centrifugal separation. The adsorption of the dissolved pigment on the activated carbon or by the technique of ion column chromatography is about the only conceivable means. In the fields specializing in the prevention of environmental pullution, removal, decolorization, and deodorization of decomposed substances of carbon and other origins which are responsible for BOD (biochemical oxygen demand) constitute three major problems At present, the method for removal of substances causing unusual rise of BOD by the use of activated sludge, for example, has substantially reached the stage of perfection. The method of activated sludge, however, is next to totally incapable of decolorizing such dissolved substances.

In the circumstances, colored plant effluents have been disposed of by a method which comprises diluting such a plant effluent with a huge volume of water and discarding the diluted effluent into a nearby body of water and colored plant effluents and fermentation broths have been disposed of by a method which comprises concentrating such a colored waste water through evaporation of water at the expense of huge energy and either transporting the concentrate aboard by ship to be discarded in the open sea or consuming the concentrate by incineration. The method resorting to the disposal in the open sea is nothing more than an attempt to eliminate the residual waste in a manner invisible to the general public. When the environmental pollution is viewed on the global scale, this method merely serves the purpose of diffusing the waste thinly and widely over the entire surface of the earth. Thus, this method in effect is contributing to scattering the colored waste at random.

None of these conventional methods, therefore, is useful for efficient removal of soluble pigments from aqueous solutions.

The appreciation of this true status of affairs has led the inventors to form a theory that when the dissolved pigment is flocculated and precipitated in the aqueous solution and then the precipitate is separated through solid-liquid separation from the aqueous solution, the floccules of precipitated pigment can be collected and disposed of by incineration and that this disposal ought to prove highly advantageous from the economic point of view. With this theory in mind, the inventors have made various studies in search of a safe method for removing the soluble pigment without entailing the possibility of inducing secondary pollution of the environment. They have consequently found that the product of microorganic culture formerly developed by the inventors as a preparation for flocculating substances suspended in water (Japanese Patent Publication SHO No. 56(1981)-39633) manifests an outstanding effect in flocculating and precipitating such soluble pigments as have been unremovable from aqueous solutions by the conventional method like centrifugal separation. This invention has been perfected as the result.

OBJECT AND SUMMARY OF THE INVENTION

An object of this invention is to provide a preparation for treating an aqueous solution of a soluble pigment thereby effecting selective and quick precipitation of the dissolved pigment in the aqueous solution and a method for the treatment by the use of this preparation.

To be specific, this invention is directed to effecting quick precipitation of the dissolved pigment in an aqueous solution by adding the product of culture of a microorganism belonging to genus Rhodococcus in either an unaltered form or a processed form to the aqueous solution for contact with the dissolved pigment in the presence of an inorganic salt.

Since this invention obtains flocculation and precipitation of the dissolved pigment in the aqueous solution merely by adding the product of microorganic culture in conjunction with an inorganic salt to the colored aqueous solution, the operation of selectively concentrating the floccules of precipitated pigment and disposing of the concentrate by incineration can be carried out easily. This invention, therefore, precludes the otherwise inevitable pollution of the environmert owing to the disposal of the colored aqueous solution.

The above and other objects and features of the invention will become more apparent from the following detailed description with reference to the accompanying drawings.

DETAILED DESCRIPTION OF THE PREFERRED EMBODIMENTS

First, the microorganism to be used in working the present invention will be described. The microorganisms usable for the purpose of this invention are bacteria belonging to genus Rhodococcus. Typical strains usable preferably herein include *Rhodococcus erythropolis* (Old name: *Nocardia erythropolis*) KR-S-1 strain (FERM P 3530) and *Rhodococcus erythropolis* (Old name: *Nocardia etythropolis*) KR-256-2 strain (FERM P 3923). In 1980, the species formerly called as *Nocardia erythropolis* was reclassified under the new name of *Rhodococcus erythropolis* by the International Committee on Nomenclature of Bacteria. The former strain was deposited with the Fermentation Research Institute, Agency of Industrial Science and Technology on Apr. 19, 1976 and the latter strain was deposited with the same Institute on Feb. 9, 1977. These strains are disclosed in U.S. Pat. No. 4,332,904 and Japanese Patent Publications No. SHO 56(1981)-29598 and No. SHO 56(1981)-39633 and are both available from the Institute.

The culture medium suitable for the strains mentioned above is composed of carbon sources such as glucose and fructose, inorganic nitrogen sources such as urea and ammonium sulfate, and organic nitrogen sources such as yeast extract and also contains nutritional sources such as inorganic salts and vitamins. The culture is generally carried out at a starting pH in the range of 4 to 11 at temperatures in the range of 20° to 40° C., with the medium kept stirred for aeration. In this culture, the amount of air supplied to the medium is desired to be such that the ratio of the amount of air to that of the medium will be not more than 1. This culture terminates in about 3 days' to 1 week's time to give a desired product of culture. This product of culture is centrifuged to remove spent cells and obtain a supernatant. This supernatant is treated with ethanol for precipitation and then with 0.8-saturation ammonium sulfate for flocculation of the produced precipitate. The flocculates are separated and purified to give riseto a purified product of culture.

The purified product of culture which is obtained from the product of microorganic culture as described above has the following physicochemical properties.

Figure 1A:
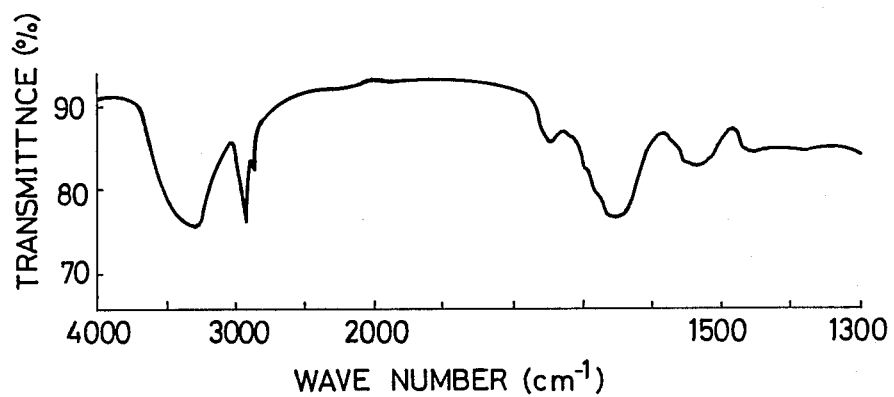
FIG. 1 is a graph showing an infrared absorption spectrum of a purified product of microorganic culture of the present invention.
Figure 1B:
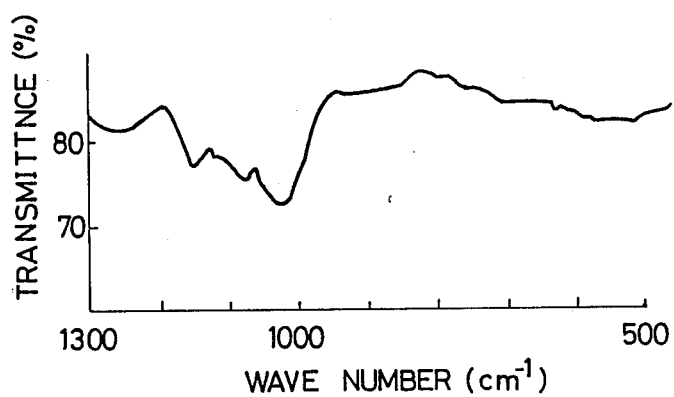

1. Color of substance: White
2. Temperature of carbonization: 244° to 265° C. (temperature increasing rate: 2° C./minute)
3. Elementary analyses:
   C: 44.94%
   H: 65.5%
   O: 44.09%
   N: 4.42%
4. Solubility: soluble in water and insoluble in organic solvents such as acetone and alcohol.
5. Infrared absorption:
   The spectrum of this substance is shown in FIG. 1; FIG. 1(a) represents a part of the spectrum covering the wave numbers in the range of 4,000 to 1,300 and FIG. 1(b) a part of the spectrum covering the wave numbers below 1,300. It is noted from the graphs that the OH absorption of carbohydrate appears near 3,300 cm$^{-1}$, the CH, CH$_2$ absorption of carbohydrate near 2,950 cm$^{-1}$, the CONH absorption of peptide and amino acid near 1,630 to 1,680 cm$^{-1}$, and the absorption pattern peculiar to polysaccharides near 800 to 1,200 cm$^{-1}$.

Figure 2:
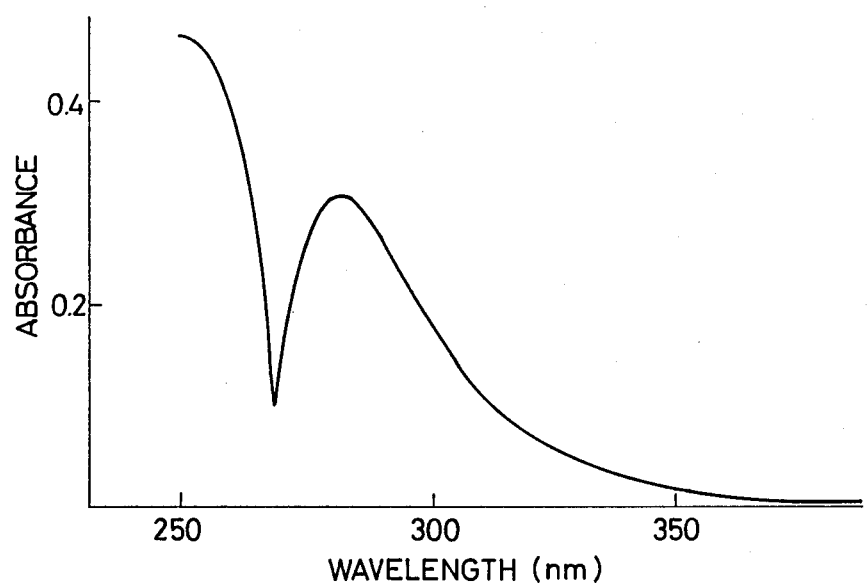
FIG. 2 is a graph showing an ultraviolet absorption spectrum of the same purified product of microorganic culture of the present invention.

From the absorption spectrum, this substance is inferred to have sugars (polysaccharides) and amino acids (proteins and/or peptides) as its components.
6. Molecular weight:
   Number average molecular weight —4,301 (reduced as proteins)
   Weight average molecular weight —20,257 (same as above)
   This measurement was obtained by the method using the aqueous GPC (high-speed liquid chromatography). The apparatus to be used was a high-speed liquid chromatogram, Waters ALC/GPG type. The sensor was a variable wavelength detector, Shimadzu SPD-1 type, operated at a wavelength of 220 nm. The column was a TSKG2000SW$^-$ and the mobile phase was moved with 1/15 M phosphate buffer, pH 7.0, 0.1 M—KCL.
7. Specific rotation:
   $[\alpha]_{5893}^{20}$ (phosphate buffer)=0°
   When a sample, 60 mg/6 ml in (1/15 phosphate buffer, pH 7, 0.1 M—KCL), was tested for specific rotation at a temperature of 20° C. with a polarimeter, Karl Zeiss 0.005° type, it showed a rotation of +0.01°. Since the reading error was within ±0.02°, $[\alpha]=0$ was fixed.
8. Ultraviolet absorption spectrum (u, v):
   The spectrum of this substance is shown in FIG. 2. It is noted from the graph that this substance possesses a zone of absorption at 280 nm, indicating that this substance possesses proteins (or peptides) as its components.
9. Color reaction:
   When this substance was subjected to the xanthoproteic reaction, it assumed a yellow color, indicating that this substance possesses proteins (or peptides) as its components.
   When it was subjected to the anthrone reaction (reaction of saccharides), it assumed a green color, indicating that this substance possesses saccharides as its components.
   From these results, the substance is inferred to be polysaccharic proteins (or peptides).
10. Acidity, alkalinity, or neutrality:
    This substance was found to possess pH 7.5, indicating that it is a neutral substance.

Based on the physicochemical properties shown above, the purified product of microorganic culture is inferred to comprise polysaccharic proteins having sugars (polysaccharides) and amino acids (proteins and/or peptides) as principal components.

Not only the purified product of microorganic culture mentioned above but also the crude product of culture and the product of culture containing spent cells (hereinafter referred to collectively as "product of microorganic culture") can be used in working the present invention.

The inorganic salt which constitutes one of tne components of the preparation of this invention for bio-precipitation is desired to be capable of forming a ation, preferably a cation possessing a valency of at least 2, in water. For example, calcium chloride which produces a divalent ion and aluminum chloride which produces a trivalent ion can be used advantageously. The amount of this inorganic salt to be added is not less than 100 ppm. Specifically, it is fixed, depending on the kind of the soluble pigment in the aqueous solution under treatment and the concentration of the dissolved solvent in the aqueous solution.

Typical examples of the soluble pigment subjected to the treatment contemplated by the present invention include melanoidin type pigments such as the black pigment which results from the combination of amino acids and reducing sugars formed in the residue of distillation during the fermentation of alcohol and the black pigment which originates inamino acids possessing benzene rings and occurring in molasses, various kinds of soluble pigments, and colored pigments originating in lignin and occurring in the production of pulp. Generally, the present invention can be advantageously worked as in the treatment of various waste liquids such as excrements emanating from live-stock farms. Further, pigmented liquids such as, for example, black ink which have heretofore been regarded as sparingly separable blends can be effectively treated by this invention to separate pigments selectively as precipitated floccules and produce nearly transparent supernatants.

Now, the removal of a soluble pigment from an aqueous solution to be effected by this invention will be described. A given aqueous solution containing a soluble pigment in a dissolved state is intimately mixed with the product of microorganic culture and the inorganic salt. A preparation obtained in advance by mixing the product of microorganic culture with the inorganic salt in a prescribed ratio may be mixed with the aqueous solution instead.

The temperature of the treatment is not specifically limited. The pH value of the liquid under treatment is desired to fall in the range of neutrality to slight alkalinity.

When the aqueous solution subjected to treatment is intimately mixed with the product of microorganic culture and the inorganic salt and then eft standing, the pigment dissolved in the aqueous solution begins to flocculate and precipitate and the upper portion of the aqueous solution gains gradually in transparency.

Although the duration of this standing is variable with the kind of the pigment dissovled in the aqueous solution, about 5 to 60 minutes' time suffices for the standing. Addition of a minute amount of a suspension aid such as kaolin to this aqueous solution enhances the speed of flocculation and precipitation of the pigment dissolved therein.

When a plant effluent containing a soluble pigment in a large amount is to be treated, this treatment can be carried out economically by an on-site type system such that a fermentation tank for the microorganism is installed at the site of discharge of the plant effluent and the product of microorganic culture is fed out of the fermentation tank and thrown into the out-flowing plant effluent.

The amount of the product of microorganic culture to be added to the aqueous solution under treatment is at least 0.5 ppm. The smallest effective amount of the product of microorganic culture to be added is fixed in due consideration of the kind and concentration of the soluble pigment involved. The amount of the inorganic salt to be added is in the range of 10 to 20 times the amount of the product of microorganic culture menticned above. The most economical amount is to be fixed, again depending on the kind and concentration of the soluble pigment dissolved in the aqueous solution.

The pigment precipitated in consequence of the treatment mentioned above separates itself from the supernatant and forms a layer of precipitated pigment. From this layer of precipitated pigment, only the pigment component is isolated by the method of centrifugal separation, the method of filtration, or the method of flocculating compression floatation. When this pigment component originates in the field of environmental pollution, it is diposed of as by incineration. When it originates in fields other than that of environmental pollution, it may be put to use again.

As described above, the present invention enables the soluble pigment, a substance heretofore regarded as hardly separable by the conventional method, to be easily removed. When it is applied to the treatment of a plant effluent having a soluble pigment of varying nature dissolved therein, the plant effluent is converted into clear waste water and is prevented from polluting the environment. Now the present invention will be described more specifically below with reference to working examples. It should be noted that this invention is not limited to these examples.

EXAMPLE 1

In 1 liter of distilled water, 10 g of glucose, 2 g of $KH_2PO_4$, 5 g of $K_2HPO_4$, 0.2 g of $MgSO_4$, 0.5 g of urea, and 0.5 g of yeast extract were dissolved. The culture medium thus prepared was adjusted to pH 7.5. A portion, 100 ml, of this culture medium was placed in an Erlenmeyer flask having an inner volume of 500 ml and sterilized in an autoclave at 120° C. for 15 minutes. The sterilized culture medium in the flask, with one platinum loop full of a strain of Rhodococcus erythropolis (FERM P 3530) inoculated thereto, was shaken-cultured at 30° C. with a rotary shaker for 4 days, to give rise to a product of culture. This product of culture was cold centrifuged (10,000 g×10 min.) to remove spent cells and admixed with ammonium sulfate up to 0.8 saturation, and left standing overnight at 5° C. to effect eduction of ammonium sulfate and give rise to a precipitated phase. This precipitated phase was dissolved in distilled water and dialyzed against distilled water with the aid of a bisquing tube for expulsion of ammonium sulfate. This treatment was repeated four more times. The dialyzate consequently obtained was freeze dried to expel the water and obtain a dry purified product of culture at a rate of 10 mg per 100 ml of the culture broth.

A mixture of 97 ml of waste pigment solution with 2 ml of an aqueous 1% calcium chloride solution and a mixture of 97 ml of the same waste pigment solution with 2 ml of an aqueous 1% aluminum chloride solution were prepared. The mixtures, severally admixed with 1 ml of an aqueous solution containing 0.1 mg of the aforementioned purified product of culture, were stirred and then left standing at rest for 5 minutes. In each of the mixtures, the dissolved pigment formed visually discernible floccules and settled down. The treated liquids were tested for transparency by measurement of absorbance.

The determination of transparency in terms of absorbance was carried out as follows. The treated liquid was admixed with a given substance and stirred and left standing. Then, the supernatant which was consequently formed was tested for absorbance with a spectrophotometer. (Depending on the kind of the soluble pigment involved, the mixture of the treated liquid with the added substance was centrifuged immediately after reaction (1,000 g×1 sec.) without being left standing in advance and the resulting supernatant was tested for absorbance.) The wavelength to be used for the determination of the absorbance was fixed by such factors as the maximum absorption wavelength of the soluble pigment involved.

For comparison, the waste pigment solution per se, a mixture of the waste pigment solution with calcium chloride, a mixture of the waste pigment solution with aluminum chloride, and a mixture of the waste pigment solution with an aqueous solution containing the purified product of culture were prepared, similarly stirred, and left standing for 5 minutes. The resulting supernatants were tested for absorbance. Since the waste solution ( possesses a largest absorption wavelength of 425 nm, the magnitudes of absorbance of the treated liquids were reported as based on the wavelength of 425 nm. The results of the test of the treated liquids for absorbance were as shown in Table 1.

It is noted from the table that when the inorganic salt and the product of microorganic culture were independently added, the respective treated liquids showed practically the same magnitudes of absorbance as when neither of them was added and that when the inorganic salt and the product of microorganic culture were jointly added, the pigment was flocculated and precipitated and the resulting supernatant showed a greatly improved transparency.

TABLE 1

|  | Absorbance (O.D.$_{425}$) of treated (after 5 minutes) liquid |
| --- | --- |
| (This invention) | |
| Waste pigment solution + $Ca^{2+}$ + product of microorganic culture | 0.101 |
| Waste pigment solution + $Al^{3+}$ + product of microorganic culture | 0.102 |
| (Control) | |
| Waste pigment solution | 1.382 |
| Waste pigment solution + $Ca^{2+}$ | 1.378 |
| Waste pigment solution + $Al^{3+}$ | 1.380 |
| Waste pigment solution + product of microorganic culture | 1.375 |

EXAMPLE 2

Fermentation of alcohol is effected with an yeast in a culture medium using waste molasses as a nutrient source. The residue which remains after the alcohol is separated by distillation is called as an "alcohol fermentation slop". The alcohol fermentation slop originating in waste molasses, during the course of fermentation and distillation, forms a persistent soluble pigment called a "melanoidin pigment". The melanoidin pigment, which is a soluble blakish brown pigment, falls among those coloring matters which are notorious for their obstinacy in defying all attempts at removal thereof from water despite all known treatments.

An alcohol fermentation slop containing this melanoidin pigment was adjusted to pH 8 and then centrifuged (10,000 g×10 min.) for removal of solid components. A portion, 90 ml, of the alcohol fermentation slop containing the soluble melanoidin was intimately mixed with 5 ml of an aqueous 10% calcium chloride solution and 5 ml of an aqueous solution containing the same product of microorganic culture as obtained in Example 1 (in a ratio of 0.1 mg of the product per ml of the solution). The resulting mixed liquid was adjusted to pH 8 and left standing at rest for one hour. The supernatant part of the mixed liquid which was formed after one hour's standing was tested for absorbance at a wavelength of 550 nm and the volume of the precipitated portion (%) was measured and reported as activity of decolorization. The results were as shown in Table 2.

It is noted from this table that this invention was effective in causing efficient flocculation and precipitation of the melanoidin pigment, a substance heretofore regarded as sparingly separable by the conventional treatment, in the alcohol fermentation slop. The table also shows the results of the same test performed on a fermentation slop in an untreated form and a fermentation slop treated by sole addition of calcium chloride.

TABLE 2

|  | Treated liquid | | |
| --- | --- | --- | --- |
|  | Volume of precipitated portion (%) | Absorbance (O.D.$_{550}$) | Ratio of decolorization |
| Alcohol fermentation slop | 0 | 2.90 | 0 |
| Alcohol fermentation slop + $Ca^{2+}$ | (+) | 2.90 | 0 |
| Alcohol fermentation slop + $Ca^{2+}$ + product of microorganic culture | 11 | 0.75 | 74 |

EXAMPLE 3

The spent liquor of pulp, unlike the alcohol fermentation slop in composition, is said to have a soluble pigment composed preponderantly of a lignin type pigment extracted during the course of production of paper from wood. The spent liquor of pulp occurs in two forms; the liquor called "black liquor" and the liquor called "bleached alkali liquor". Because of the persistent colors assumed, these two liquors both must be prevented from flowing out of pulp plants. Thus, the spent liquor of pulp is counted among those plant effluents which elude all attempts at removing coloring matter to the greatest extent.

Portions, 90 ml each, of these two spent liquors of pulp were severally stirred with 5 ml of an aqueous 10% calcium chloride solution and 5 ml of an aqueous solution containing the same product of microorganic culture as obtained in Example 1 (at a ratio of 0.1 mg of the product per ml). The mixed liquids consequently obtained were adjusted to pH 7.5 and left standing for one hour. The supernatents formed after the standing were tested for absorbance at a wavelength of 415 nm.

For the purpose of promoting the flocculation and precipitation of the soluble pigment, to the bleached alkali liquor, kaolin was added besides the calcium chloride and the aqueous solution of the product of culture in an amount to give a final concentration of 500 ppm. The treated liquids were tested. The results were as shown in Table 3.

TABLE 3

|  | Treated liquid | | |
| --- | --- | --- | --- |
|  | (Black liquor) Absorbance (O.D.$_{415}$) | (Bleached alkali liquor) | |
|  | | Absorbance (O.D.$_{415}$) | Volume of precipitated portion (%) |
| Spent liquor alone | 2.34 | 0.363 | 0 |
| Spent liquor + $Ca^{2+}$ | 2.28 | 0.363 | 0 |
| Spent liquor + $Ca^{2+}$ + product of microorganic culture | 0.90 | 0.246 | 64 |
| Spent liquor + $Ca^{2+}$ + product of microorganic culture + kaolin | — | 0.105 | 15 |

It is noted from Table 3 that, by the treatment of this invention, the black color of the black liquor from pulp and the brown color of the bleached alkali liquor both thinned until decolorization. In the system additionally incorporating the suspending substance, the floccules of the pigment grew to a larger size and the speed of flocculation and precipitation was increased notably and the treated liquids acquired improved transparency.

EXAMPLE 4

The waste molasses is the liquid which remains after refined sugar is produced from the decoction of sugar canes. Since this waste molasses still contains a fair amount of sugar and a large amount of minerals, it finds popular utility as an inexpensive raw material for the culture medium of microorganisms. At present, it constitutes an economical foundation for the fermentation industry.

Unfortunately, the waste molasses is deeply blackish and cannot be easily decolorized by the conventional method.

The present invention was ried on the spent liquor of waste molasses which remained after culture of yeast in a medium using waste molasses as a nutrient source. A portion, 95 ml, of the spent liquor of waste molasses was mixed with 2.5 ml of an aqueous 10% calcium chloride solution and 2.5 ml of an aqueous solution containing the same product of microorganic culture as obtained in Example 1 (in a ratio of 0.1 mg of product per ml). The resulting reaction system was adjusted to pH 8. In the system, formation of minute floccules was clearly visible. Since the floccules took much time in setting, the system was centrifuged (1,000 g × 1 sec to accelerate the precipitation. The supernatant consequently formed was tested for absorbance at 550 nm and the volume of the precipitated portion (%) was measured. The results were as shown in Table 4.

It is noted from Table 4 that when the aqueous solution of the product of microorganic culture was added in the presence of the inorganic salt, the soluble pigment originating in the waste molasses formed floccules and separated from the aqueous medium. As a result, the blackish brown color of the spent liquor thinned and the supernatant gained in transparency.

TABLE 4

| — | Supernatant formed after centrifugation Absorbance (O.D.$_{415}$) | Volume of precipitated portion (%) |
|---|---|---|
| Spent liquor of waste molasses | 5.00 | 0 |
| Spent liquor of waste molasses + Ca$^{2+}$ | 4.90 | (+) |
| Spent liquor of waste molasses + Ca$^{2+}$ + product of microorganic culture | 2.80 | 5 |

EXAMPLE 5

Figure 3:
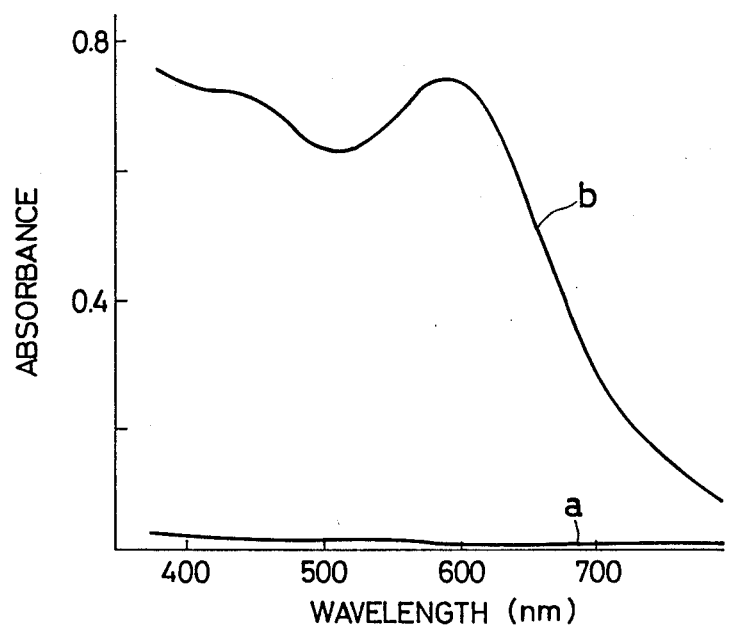
FIG. 3 is a graph showing an absorption spectrum of black ink treated by the present invention.

A solution prepared in advance by dissolving 0.5 mg of the same product of microorganic culture as obtained in Example 1 and 0.05 g of calcium chloride in 10 ml of distilled water was mixed with 90 ml of a commercially available black ink (product of Pilot Pen Co., Ltd., Japan). After the mixing, the black ink immediately produced floccules and the floccules began to sink slowly. The resulting mixture was left standing for one hour. The supernatant consequently formed was diluted with distilled water to 200 times the original volume. The diluted supernatant was processed to produce an absorption spectrum in a wavelength zone of 370 to 800 nm. For comparison, the same black ink was left standing alone for one hours. The supernatant consequently formed was diluted similarly to 200 times the original volume and processed similarly to produce an absorption spectrum. The results were as shown in a graph of FIG. 3. In the graph, the curve "a" represents the absorption spectrum of the diluted black ink treated by the present invention and the curve (b) that of the control. It is clearly noted from this graph that the black ink showed an absorption peak near a wavelength, of 600 nm and an absorption shoulder peak in the neighborhood of. wavelengths of 440 to 450 nm, whereas the liquid treated by the present invention was such that the soluble substance (pigment) formed floccules and settled and the supernatant showed virtually no absorption.

The procedure of this example was faithfully repeated, except that the amount of the product of microorganic culture added was varied in the range of 0.01 mg to 5 mg. The diluted supernatants of the black ink were processed tq produce absorption spectra at a wavelength of 600 nm. The results were as shown in Table 5.

TABLE 5

| Final concentration of flocculant (mg/liter) | Clarification of supernatants after 1 hr. (O.D.$_{660}$) |
|---|---|
| 0 (control)* | 148 |
| 0.1 | 120 |
| 0.5 | 8 |
| 1 | 0.5 |
| 5 | 0.2> |
| 10 | 0.2> |
| 50 | 0.2> |

*Total organic carbon of control solution was 28,620 ppm.

From Table 5, it is noted that in the case of this example, the amount of the product of microorganic culture to be added is desired to exceed 0.5 mg per liter.

Then, the procedure described above was faithfully repeated, excet that the amount of the product of microorganic culture to be added was fixed at 0.5 mg and that the amount of calcium chloride to be added was varied in the range of 0 to 0.5 g. The diluted supernatants of black ink consequently obtained were processed to produce absorption spectra at a wavelength of 600 nm. The results were as shown in Table 6.

TABLE 6

| Conc. of CaCl$_2$ (g/liter) | Clarification of Supernatant after 1 hour O.D.$_{660}$ |
|---|---|
| 0 | 148 |
| 0.05 | 140 |
| 0.1 | 56 |
| 0.2 | 10 |
| 0.5 | 0.2 |
| 1.0 | 0.2 |
| 2.5 | 0.2 |
| 5.0 | 0.2 |

It is noted from the table that the amount of CaCl$_2$ to be added has only to reach 0.2 g per liter to be substantially sufficient.

In the example cited above, calcium chloride was used as an inorganic salt. When this procedure was repeated using aluminum chloride in place of calcium chloride, there were obtained similar results.

EXAMPLE 6

In a culture medium of the same composition as in Example 1, a strain, KR-256-2 of *Rhodococcus erythropolis* (FERM P 3923) was cultured under the same conditions. From the resulting culture broth, a dry purified product of culture was obtained in a rate of 8 mg per 100 ml of the culture broth.

An intimate mixture of 0.5 mg of the aforementioned product of microorganic culture with 0.05 g of calcium chloride was added each to 100 ml of an aqueous solution of a water-soluble bicolor. tar type pigment, fast green FCF, i.e. (4]{[4-(N-ethyl-methasulfobenzylamino)-phenyl]( 4-hydroxy-2-sulfoniumphenyl)-methylene}-[1-(N-ethyl-N-metasulfobenzyl-$\Delta^{2,5}$-cyclohexadieneimine]-disodium salt and to 100 ml of an aqueous solution of rhodamine B, [(9-ortho-carboxyphenyl-6-diethylamino-3-ethylamino-3-isoxanthene-3-ethochloride]. The resulting mixtures were adjusted to pH 8.0 and then left standing at rest for 30 minutes. The supernatant of the fast green, FCF, was tested for absorbance at a wavelength of 625 nm, at which the maximum absorption peak is shown for the fast green FCF. The supernatant of the rhodamine B was tested for absorbance at a wavelength of 553 nm, at which the maximum absorption peak is shown for the rhodamine B. The former supernatant showed an absorbance of 0.423 as compared with the absorbance 0.556 shown by the untreated supernatant and the latter supernatant showed an absorbance of 0.367 as compared with the absorbance 0.427 shown by the untreated supernatant. These decreases of the magnitudes of absorbance evince removal of the dissolved pigments.

EXAMPLE 7

A brown refuse (pH 9.5) containing the excrement emanating from a pigsty which had been deprived of solid components by centrifugation was adjusted with hydrochloric acid to pH 7.0. A portion, 80 ml, of this brown refuse was admixed with 10 ml of an aqueous 1% calcium chloride solution and a varying amount (1 ml, 5 ml, or 10 ml) of the unpurified product of microorganic culture of Example 1 and then left standing for 10 minutes and tested for absorbance and for the volume of precipitation of pigment. They were also tested for total organic carbon with a Beckman TOC analyzer (Model 915-B) and for total nitrogen by the Kjeldahl method. For comparison, the untreated refuse and the refuse admixed with 10 ml of an aqueous solution of calcium chloride were similarly left standing for 10 minutes and subsequently tested. The results were as shown in Table 7. It is noted from this table that the refuses using 5.0 ml and 10 ml of the product of culture brought out precipitation of pigment and the magnitudes of absorbance showed by the resulting treated liquid were not more than 0.02. These treated liquids were found by observation with the unaided eye to be colorless and transparent.

TABLE 7

|  | Precipitate volume (%) | Supernatant after 10 min. | | |
|---|---|---|---|---|
|  |  | TOC (ppm) | TN (mg/liter) | Clarification (O.D.$_{660}$) |
| Waste water | 0 | 1420 | 420 | 8.60 |
| Waste water + Ca$^{2+}$ | 0 | 1420 | 420 | 8.60 |
| Waste water + Ca$^{2+}$ + culture broth |  |  |  |  |
| 1.0 ml | 3 | 1250 | 310 | 6.90 |
| 5.0 ml | 11 | 425 | 215 | 0.02> |
| 10.0 ml | 13 | 504 | 213 | 0.02> |

What is claimed is:

1. A method for the treatment of an aqueous solution of a soluble pigment for the removal of said soluble pigment from said aqueous solution, which method comprises adding to said aqueous solution of said soluble pigment in the presence of an inorganic salt the product of microorganic culture obtained by culturing a bacterium belonging to genus Rhodococcus, intimately mixing said aqueous solution with said product of microorganic culture, allowing the resulting mixture to stand at rest thereby causing said soluble pigment to precipitate, and separating the precipitated pigment from said aqeorus solution.

2. The method according to claim 1, wherein said bacterium of genus Rhodococcus is the strain of a species erythropolis KR-S-1 (FERM P 3530).

3. The method according to claim 1, wherein said bacterium of genus Rhodococcus is the strain of a species erythropolis KR-256-2 (FERM P 3923).

4. The method according to claim 1, wherein said product of microorganic culture contains the culture medium in which the microorganism has been cultured.

5. The method according to claim 1, wherein said product of microorganic culture contains an aggregate obtained by isolating and purifying the culture medium in which the microorganism has been cultured.

6. The method according to claim 1, wherein said inorganic salt is calcium chloride.

7. The method according to claim 1, wherein said inorganic salt is aluminum chloride.

8. The method according to claim 1, wherein the amount of said inorganic salt to be added is about 10 times the amount of said product of microorganic crlture.

9. The method according to claim 1, wherein the concentration of said product of microorganic culture is not less than 0.17 ppm, based on 10,000 ppm of said soluble pigment as total organic carbon.

10. A preparation for the treatment of an aqueous solution of a soluble pigment for the removal of said soluble pigment from said aqueous solution, which comprises the product of a microorganic culture resulting from the culture of a bacterium of genus Rhodococcus and an inorganic salt.

11. The preparation according to claim 10, wherein said bacterium of genus Rhodococcus is the strain of a species erythropolis KR-S-1 (FERM P 3530).

12. The preparation according to claim 10, wherein said,bacterium of genus Rhodococcus is the strain of a species erythropolis KR-256-2 (FERM P 3923).

13. The preparation according to claim 10, wherein said inorganic salt is calcium chloride.

14. The preparation according to claim 10, wherein said inorganic salt is aluminum chloride.

15. The preparation according to claim 10, wherein the amount of said inorganic salt to be added is about 10 times the amount of said product of microorganic culture.

* * * * *